US011897125B2

(12) United States Patent
Kang et al.

(10) Patent No.: US 11,897,125 B2
(45) Date of Patent: Feb. 13, 2024

(54) SPRING ARRAY DEVICE FOR VERIFYING RELIABILITY AND ACCURACY OF MECHANICAL IMPEDANCE ESTIMATING ROBOT AND CONNECTING STRUCTURE THEREBETWEEN

(71) Applicant: UNIST(ULSAN NATIONAL INSTITUTE OF SCIENCE AND TECHNOLOGY), Ulsan (KR)

(72) Inventors: Sang Hoon Kang, Ulsan (KR); Hyunah Kang, Ulsan (KR)

(73) Assignee: UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 1039 days.

(21) Appl. No.: 16/788,263

(22) Filed: Feb. 11, 2020

(65) Prior Publication Data
US 2020/0331154 A1 Oct. 22, 2020

(30) Foreign Application Priority Data

Apr. 18, 2019 (KR) ........................ 10-2019-0045536

(51) Int. Cl.
*B25J 19/00* (2006.01)
*A61B 5/00* (2006.01)
(Continued)

(52) U.S. Cl.
CPC ......... *B25J 19/0095* (2013.01); *A61B 5/4528* (2013.01); *A61B 2560/0223* (2013.01);
(Continued)

(58) Field of Classification Search
CPC .......... G05B 2219/39338; G05B 2219/39343; G05B 2219/39464; G05B 2219/39492;
(Continued)

(56) References Cited

U.S. PATENT DOCUMENTS

2001/0038376 A1* 11/2001 Sato ...................... G06F 3/0346
345/156
2005/0024331 A1* 2/2005 Berkley ................. A61B 34/71
345/157
(Continued)

FOREIGN PATENT DOCUMENTS

DE 3606685 A1 * 9/1987 ............... G01L 5/16
JP 2001-282448 A 10/2001
(Continued)

OTHER PUBLICATIONS

IEEE, Engineering 360 Learn More About Bolts, 2018 (Year: 2018).*
(Continued)

*Primary Examiner* — David L Singer
(74) *Attorney, Agent, or Firm* — Revolution IP, PLLC

(57) ABSTRACT

A 3D spring array device includes: a fixed body having an internal space therein; a moving body positioned in a center of an x-y-z orthogonal coordinate system in the internal space, wherein the moving body is configured to be fastenable to the end effector of the mechanical impedance estimating robot; and a first spring, a second spring, a third spring, a fourth spring, a fifth spring, a sixth spring, a seventh spring, and an eighth spring and configured to connect the fixed body to the moving body in the internal space.

7 Claims, 3 Drawing Sheets

(51) Int. Cl.
*G01L 1/04* (2006.01)
*G01L 5/161* (2020.01)

(52) U.S. Cl.
CPC ......... *F16F 2230/0005* (2013.01); *G01L 1/04* (2013.01); *G01L 5/161* (2013.01)

(58) Field of Classification Search
CPC ........... G05B 2219/40368; G05B 2219/40372; G05B 2219/40578; A61B 2505/09; A61B 2560/0223; A61B 5/00; A61B 5/0048; A61B 5/224; A61B 5/4528; A61B 5/458; A61B 5/6825; B25J 19/0095; F16F 2230/0005; F16F 2230/0017; F16F 3/04; G01L 1/04; G01L 5/161; G01M 1/10; G01M 99/005; G01M 99/008
See application file for complete search history.

(56) References Cited

U.S. PATENT DOCUMENTS

| | | | | |
|---|---|---|---|---|
| 2008/0150891 | A1* | 6/2008 | Berkley | G06F 3/016 345/156 |
| 2015/0190200 | A1* | 7/2015 | Courtine | A61B 5/721 604/20 |
| 2018/0085016 | A1* | 3/2018 | Kang | A61B 5/053 |

FOREIGN PATENT DOCUMENTS

| | | | | |
|---|---|---|---|---|
| KR | 10-2012-0002157 A | | 1/2012 | |
| KR | 10-2015-0017747 A | | 2/2015 | |
| KR | 101848670 B1 | * | 4/2018 | ............ B25J 9/0006 |
| KR | 10-2013854 B1 | | 8/2019 | |

OTHER PUBLICATIONS

Roberts et al., A Survey of Some Results on Spatial Stiffness Matrices, IEEE (Year: 2001).*
Stramigioli, Variable Spatial Springs for Robot Control Applications, IEEE (Year: 2001).*

* cited by examiner

SPRING ARRAY DEVICE FOR VERIFYING RELIABILITY AND ACCURACY OF MECHANICAL IMPEDANCE ESTIMATING ROBOT AND CONNECTING STRUCTURE THEREBETWEEN

CROSS-REFERENCE TO RELATED PATENT APPLICATIONS

This application claims the benefit of Korean Patent Application No. 10-2019-0045536, filed on Apr. 18, 2019, in the Korean Intellectual Property Office, the disclosure of which is incorporated herein in its entirety by reference.

BACKGROUND OF THE INVENTION

1. Field of the Invention

The present invention relates to impedance estimating robot technology and more particularly, to technology for verifying reliability and accuracy of an impedance estimating robot.

2. Description of the Related Art

Stiffness appears in joints such as the elbow of stroke patients, resulting in an increase in mechanical impedance, which is a resistance of movement to the joint. In order to rehabilitate a patient, it is necessary to measure the mechanical impedance of the joint. In general, the measurement of the mechanical impedance of the joint is performed in such a way that a measurer who is human moves a patient's joint by hand. This method may depend on the measurer's sense and thus may vary according to the measurer's skillfulness and experiences and according to times even by the same measurer and thus, there is a limitation in objective diagnosis.

In order to solve the problem according to the mechanical impedance evaluation method based on the human senses as described above, a mechanical impedance estimating robot for measuring mechanical impedance in three directions (three-dimensional (3D)) using a robot, as disclosed in Korean Patent Publication No. 10-2018-0035669, has been recently developed. The mechanical impedance estimating robot that is a robot for measuring mechanical impedance such as upper limb multi-joint for body rehabilitation includes a body connection part connected to a body such as a human hand, a driving part for driving the body connection part, a force sensor for detecting the magnitude and direction of the force applied to the body connection part, and a position sensor for detecting the position of the body connection part and calculates the mechanical impedance of a subject using data measured by the force sensor and the position sensor.

The mechanical impedance estimating robot undergoes a calibration process so as to improve the accuracy of the measured mechanical impedance and verify the reliability. It is difficult to perform calibration for 3D, and thus, a device therefor is required.

SUMMARY OF THE INVENTION

The present invention provides a three-dimensional (3D) spring array device for verifying the reliability and accuracy of a mechanical impedance estimating robot and a connecting structure therebetween.

According to an aspect of the present invention, there is provided a three-dimensional (3D) spring array device that is connected to an end effector of a mechanical impedance estimating robot so as to verify reliability and accuracy of the mechanical impedance estimating robot, the 3D spring array device including a fixed body having an internal space therein, a moving body positioned in a center of an x-y-z orthogonal coordinate system in the internal space, and at least one spring selected from a group consisting of a first spring, a second spring, a third spring, a fourth spring, a fifth spring, a sixth spring, a seventh spring, and an eighth spring and configured to connect the fixed body to the moving body in the internal space, wherein each of the first spring and the second spring is positioned to extend along a first straight line that passes through a coordinate (0, a, a) and a coordinate (0, −a, −a) in the x-y-z orthogonal coordinate system, and the first spring and the second spring are positioned at opposite sides with the moving body therebetween, and each of the third spring and the fourth spring is positioned to extend along a second straight line that passes through a coordinate (a, 0, a) and a coordinate (−a, 0, −a) in the x-y-z orthogonal coordinate system, and the third spring and the fourth spring are positioned at opposite sides with the moving body therebetween, and each of the fifth spring and the sixth spring is positioned to extend along a third straight line that passes through a coordinate (a, a, a) and a coordinate (−a, −a, −a) in the x-y-z orthogonal coordinate system, and the fifth spring and the sixth spring are positioned at opposite sides with the moving body therebetween, and each of the seventh spring and the eighth spring is positioned to extend along a fourth straight line that passes through a coordinate (a, a, 0) and a coordinate (−a, −a, 0) in the x-y-z orthogonal coordinate system, and the seventh spring and the eighth spring are positioned at opposite sides with the moving body therebetween.

According to another aspect of the present invention, there is provided a three-dimensional (3D) spring array device that is connected to an end effector of a mechanical impedance estimating robot so as to verify reliability and accuracy of the mechanical impedance estimating robot, the 3D spring array device including a fixed body having an internal space therein, a moving body positioned in the internal space and at least one spring configured to connect the fixed body to the moving body in the internal space, wherein the fixed body includes at least one spring coupling portion selected from a group consisting of a first spring coupling portion, a second spring coupling portion, a third spring coupling portion, a fourth spring coupling portion, a fifth spring coupling portion, a sixth spring coupling portion, a seventh spring coupling portion, and an eighth spring coupling portion, which are coupled to each of the at least one spring, and the fifth spring coupling portion and the sixth spring coupling portion are positioned at two vertices that are symmetrical with each other with respect to the moving body in a regular hexahedron based on the moving body, and each of the first spring coupling portion, the third spring coupling portion, and the seventh spring coupling portion is positioned in a center of three corners each being connected to one of the two vertices at which the fifth spring coupling portion is positioned in the regular hexahedron, and each of the second spring coupling portion, the fourth spring coupling portion, and the eighth spring coupling portion is positioned in a center of the three corners each being connected to the other one of the two vertices at which the sixth spring coupling portion is positioned in the regular hexahedron.

According to another aspect of the present invention, there is provided a structure for connecting a three-dimensional (3D) spring array device for verifying reliability and accuracy of a mechanical impedance estimating robot to the mechanical impedance estimating robot, wherein the 3D spring array device includes a fixed body having an internal space therein, a moving body positioned in the internal space, and at least one spring configured to connect the fixed body to the moving body, and an end effector provided in the mechanical impedance estimating robot is separably coupled to the moving body.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the configuration and operation of embodiments of the present invention will be described more fully with reference to the attached drawings.

Figure 1:
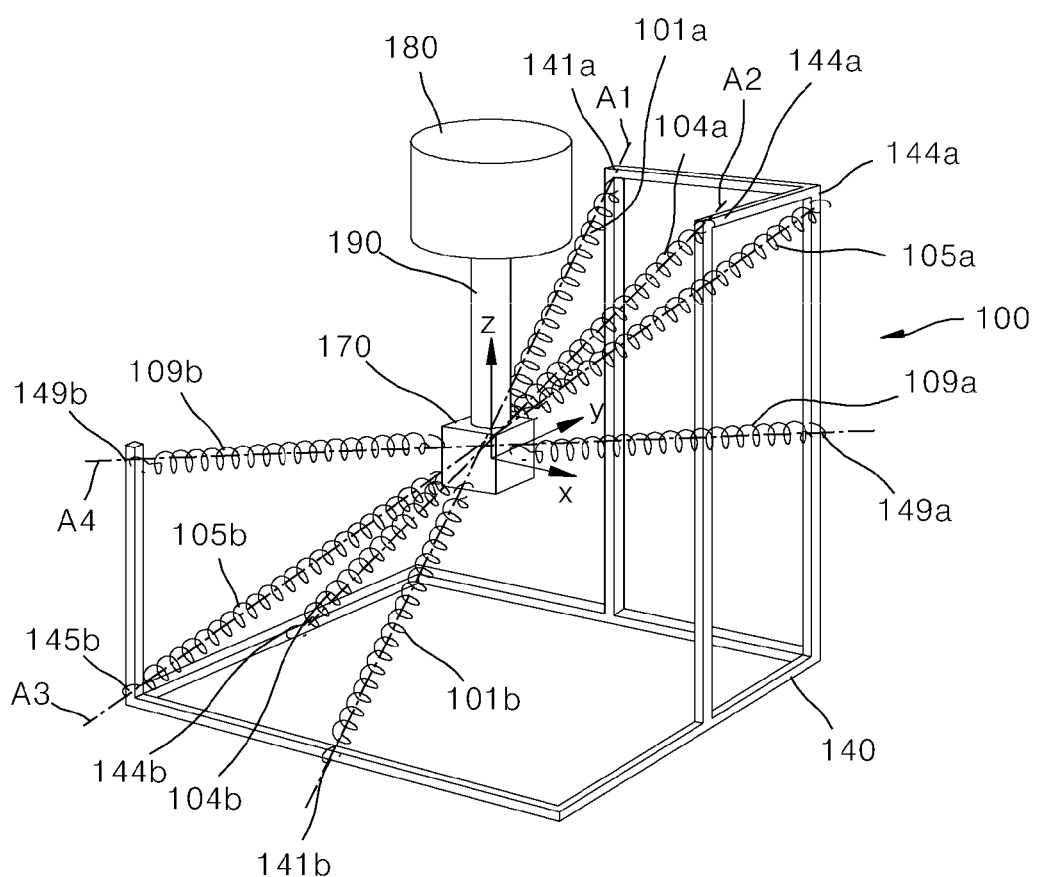
FIG. 1 is a perspective view of a three-dimensional (3D) spring array device for verifying the reliability and accuracy of a mechanical impedance estimating robot according to an embodiment of the present invention, which illustrates a state in which the mechanical impedance estimating robot is connected to a robot to be verified.
Figure 2:
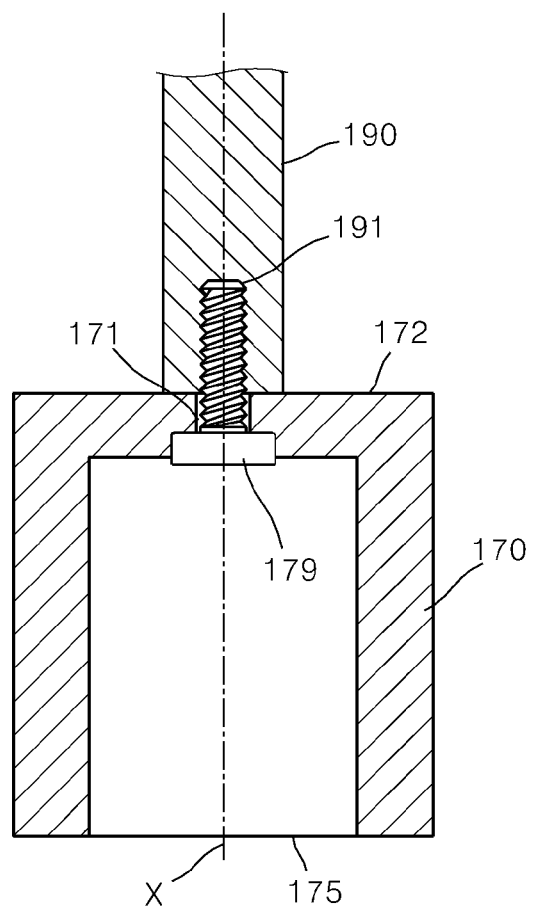
FIG. 2 is a cross-sectional view illustrating in detail a connected portion between the 3D spring array device illustrated in FIG. 3 and the robot.

FIG. 1 is a perspective view of a three-dimensional (3D) spring array device for verifying the reliability and accuracy of a mechanical impedance estimating robot according to an embodiment of the present invention, which illustrates a state in which the mechanical impedance estimating robot is connected to a robot to be verified. Referring to FIG. 1, a 3D spring array device 100 according to an embodiment of the present invention includes a fixed body 140, a moving body 170 inside the fixed body 140, and a plurality of springs 101a, 101b, 104a, 104b, 105a, 105b, 109a, and 109b, which connect the fixed body 140 to the moving body 170 inside the fixed body 140.

The fixed body 140 having a shape of an overall regular hexahedral frame that provides an empty internal space includes a plurality of spring coupling portions 141a, 141b, 144a, 144b, 145a, 145b, 149a, and 149b, to which an end of each of the plurality of springs 101a, 101b, 104a, 104b, 105a, 105b, 109a, and 109b is coupled. The fixed body 140 is installed to be fixed when an experiment for verification is performed. The moving body 170 is located in the center of the internal space of the fixed body 140.

The plurality of spring coupling portions 141a, 141b, 144a, 144b, 145a, 145b, 149a, and 149b include first, second, third, fourth, fifth, sixth, seventh, and eighth spring coupling portions 141a, 141b, 144a, 144b, 145a, 145b, 149a, and 149b. In order to explain the position of each of the plurality of spring coupling portions 141a, 141b, 144a, 144b, 145a, 145b, 149a, and 149b in detail, an x-y-z orthogonal coordinate system based on the moving body 170 will be introduced.

The first spring coupling portion 141a and the second spring coupling portion 141b are positioned at a point in which they are symmetrical with each other based on the moving body 170. In detail, the first spring coupling portion 141a and the second spring coupling portion 141b are positioned at a coordinate (0, a, a) and a coordinate (0, −a, −a) at the introduced x-y-z orthogonal coordinate system. Here, a is a positive number and is included in the internal space range of the fixed body 140. In the present embodiment, each of the first spring coupling portion 141a and the second spring coupling portion 141b is positioned in the center of two corners of the fixed body 140 having the regular hexahedral frame shape.

The third spring coupling portion 144a and the fourth spring coupling portion 144b are positioned at a point in which they are symmetrical with each other based on the moving body 170. In detail, the third spring coupling portion 144a and the fourth spring coupling portion 144b are positioned at a coordinate (a, 0, a) and a coordinate (−a, 0, −a) in the introduced x-y-z orthogonal coordinate system. In the present embodiment, each of the third spring coupling portion 144a and the fourth spring coupling portion 144b is positioned in the center of two corners of the fixed body 140 having the regular hexahedral frame shape.

The fifth spring coupling portion 145a and the sixth spring coupling portion 145b are positioned at a point in which they are symmetrical with each other based on the moving body 170. In detail, the fifth spring coupling portion 145a and the sixth spring coupling portion 145b are positioned at a coordinate (a, a, a) and a coordinate (−a, −a, −a) in the introduced x-y-z orthogonal coordinate system. In the present embodiment, each of the fifth spring coupling portion 145a and the sixth spring coupling portion 145b is positioned at two vertices of the fixed body 140 having the regular hexahedral frame shape.

The seventh spring coupling portion 149a and the eighth spring coupling portion 149b are positioned at a point in which they are symmetrical with each other based on the moving body 170. In detail, the seventh spring coupling portion 149a and the eighth spring coupling portion 149b are positioned at the coordinate (a, a, 0) and the coordinate (−a, −a, 0) in the introduced x-y-z orthogonal coordinate system. In the present embodiment, each of the seventh spring coupling portion 149a and the eighth spring coupling portion 149b is positioned in the center of two corners of the fixed body 140 having the regular hexahedral frame shape.

The moving body 170 is positioned in the internal space of the fixed body 140. In the present embodiment, it will be described that the moving body 170 is positioned in the center of the inside of the fixed body 140 having the regular hexahedral frame shape. Each of the plurality of springs 101a, 101b, 104a, 104b, 105a, 105b, 109a, and 109b is connected to the moving body 170. In the present embodiment, the moving body 170 has a regular hexahedral shape. However, in the present invention, the shape of the moving body 170 is not limited to the regular hexahedral shape. The moving body 170 is coupled to be separable from an end effector 190 of an impedance estimating robot to be verified. To this end, the moving body 170 is hollow and has a bolt hole 171 in one side wall 172. A coupling bolt 179 is coupled to a female hole 191 formed at an end of the end effector 190 of the impedance estimating robot via the bolt hole 171. For tightening and loosening of the coupling bolt 179, an opening 175 that is opposite to the bolt hole 171 is formed in the moving body 170. In order to improve the accuracy of verification, the bolt hole 171 may be positioned on a central axis line X of the moving body 170 so that the end effector 190 may be coupled to the moving body 170 on the central axis line X of the moving body 170. A sensor module 180, which includes a force sensor for sensing the force applied to the end effector 190 and a position sensor for detecting the position of the end effector 190, is coupled to the end effector 190 of the impedance estimating robot to be verified.

The plurality of springs 101a, 101b, 104a, 104b, 105a, 105b, 109a, and 109b are tension springs and include first, second, third, fourth, fifth, sixth, seventh, and eighth springs 101a, 101b, 104a, 104b, 105a, 105b, 109a, 109b. In the present embodiment, the plurality of springs 101a, 101b, 104a, 104b, 105a, 105b, 109a, and 109b are tension coil springs. However, this is just an example of a spring, and in the present invention, springs are not limited to tension coil springs.

The first spring 101a is a tension spring extending in a straight line and has both ends coupled to each of the moving body 170 and a first spring coupling portion 141a of the fixed body 140 at the coordinate (0, a, a) in the introduced x-y-z orthogonal coordinate system. The first spring 101a is positioned to pass through an original point O of the x-y-z orthogonal coordinate system that is the center of the moving body 170 and to extend along a first straight line A1 that passes through the coordinate (0, a, a).

The second spring 101b is a tension spring extending in a straight line and has both ends coupled to each of the moving body 170 and the second spring coupling portion 141b of the fixed body 140 at the coordinate (0, −a, −a) in the introduced x-y-z orthogonal coordinate system. The second spring 101b is positioned to pass through the original point O of the x-y-z orthogonal coordinate system that is the center of the moving body 170 and to extend along the first straight line A1 that passes through the coordinate (0, −a, −a).

The third spring 104a is a tension spring extending in a straight line and has both ends coupled to each of the moving body 170 and the third spring coupling portion 144a of the fixed body 140 at the coordinate (a, 0, a) in the introduced x-y-z orthogonal coordinate system. The third spring 104a is positioned to pass through the original point O of the x-y-z orthogonal coordinate system that is the center of the moving body 170 and to extend along a second straight line A2 that passes through the coordinate (a, 0, a).

The fourth spring 104b is a tension spring extending in a straight line and has both ends coupled to each of the moving body 170 and the fourth spring 144b of the fixed body 140 at the coordinate (−a, 0, −a) in the introduced x-y-z orthogonal coordinate system. The fourth spring 104b is positioned to pass through the original point O of the x-y-z orthogonal coordinate system that is the center of the moving body 170 and to extend along the second straight line A2 that passes through the coordinate (−a, 0, −a).

The fifth spring 105a is a tension spring extending in the straight line and has both ends coupled to each of the moving body 170 and the fifth spring coupled portion 145a of the fixed body 140 at the coordinate (a, a, a) in the introduced x-y-z orthogonal coordinate system. The fifth spring 105a is positioned to pass through the original point O of the x-y-z orthogonal coordinate system that is the center of the moving body 170 and to extend along a third straight line A3 that passes through the coordinate (a, a, a).

The sixth spring 105b is a tension spring extending in a straight line and has both ends coupled to each of the moving body 170 and the sixth spring coupling portion 145b of the fixed body 140 at the coordinate (−a, −a, −a) in the introduced x-y-z orthogonal coordinate system. The sixth spring 105b is positioned to pass through the original point O of the x-y-z orthogonal coordinate system that is the center of the moving body 170 and to extend along the third straight line A3 that passes through the coordinate (−a, −a, −a).

The seventh spring 109a is a tension spring extending in a straight line and has both ends coupled to each of the moving body 170 and the seventh spring coupling portion 149a of the fixed body 140 at the coordinate (a, a, 0) in the introduced x-y-z orthogonal coordinate system. The seventh spring 109a is positioned to pass through the original point O of the x-y-z orthogonal coordinate system that is the center of the moving body 170 and to extend along a fourth straight line A4 that passes through the coordinate (a, a, 0).

The eighth spring 109b is a tension spring extending in a straight line and has both ends coupled to each of the moving body 170 and the eighth spring coupling portion 149b of the fixed body 140 at the coordinate (a, −a, 0) in the introduced x-y-z orthogonal coordinate system. The eighth spring 109b is positioned to pass through the original point O of the x-y-z orthogonal coordinate system that is the center of the moving body 170 and to extend along the fourth straight line A4 that passes through the coordinate (a, −a, 0).

Figure 3:
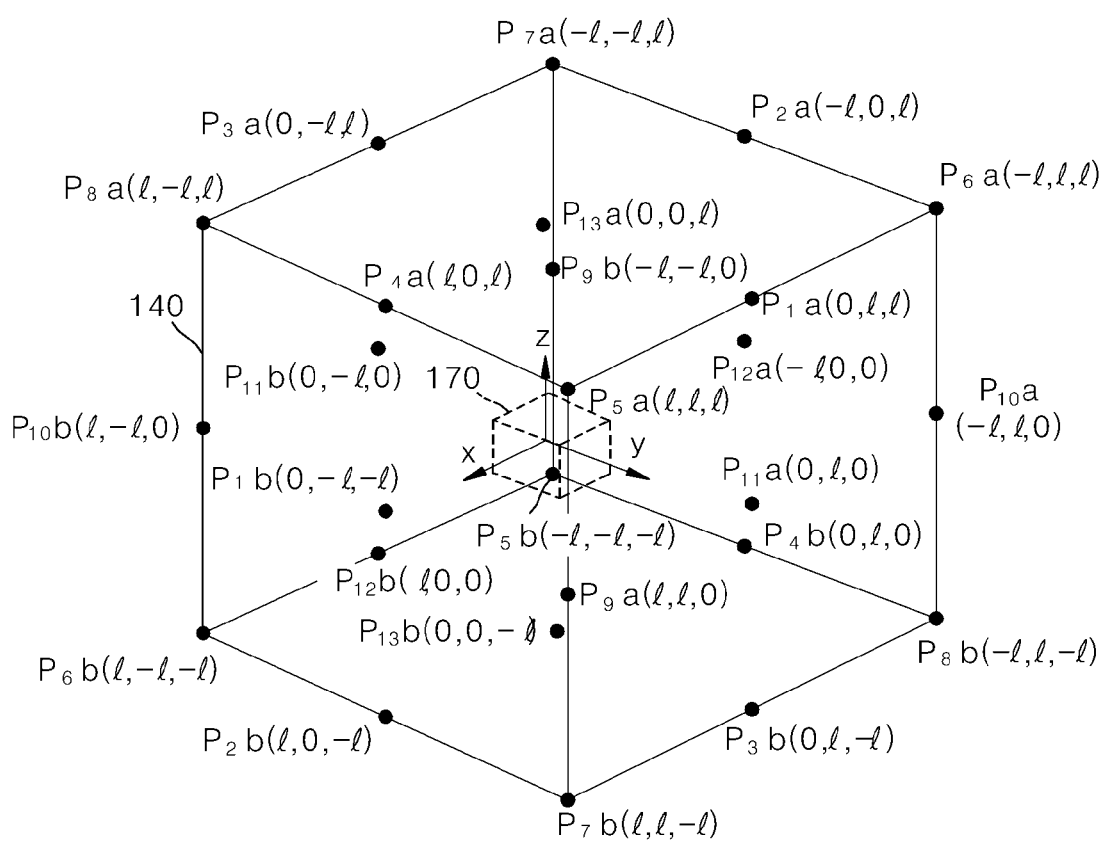
FIG. 3 is a conceptual view for explaining a procedure of selecting a spring of the 3D spring array device illustrated in FIG. 3.

FIG. 3 is a conceptual view for explaining a procedure of selecting the eighth springs 101a, 101b, 104a, 104b, 105a, 105b, 109a, 109b in the 3D spring array device 100 illustrated in FIG. 1. Hereinafter, this will be described in detail with reference to FIG. 3.

Referring to FIG. 3, a first A-point $P_{1a}$, a first B-point $P_{1b}$, a second A-point $P_{2a}$, a second B-point $P_{2b}$, a third A-point $P_{3a}$, a third B-point $P_{3b}$, a fourth A-point $P_{4a}$, a fourth B-point $P_{4b}$, a fifth A-point $P_{5a}$, a fifth B-point $P_{5b}$, a sixth A-point $P_{6a}$, a sixth B-point $P_{6b}$, a seventh A-point $P_{7a}$, a seventh B-point $P_{7b}$, an eighth A-point $P_{8a}$, an eighth B-point $P_{8b}$, a ninth A-point $P_{9a}$, a ninth B-point $P_{9b}$, a tenth A-point $P_{10a}$, a tenth B-point $P_{10b}$, an eleventh A-point $P_{11a}$, an eleventh B-point $P_{11b}$, a twelfth A-point $P_{12a}$, a twelfth B-point $P_{12b}$, a thirteenth A-point $P_{13a}$, and a thirteenth B-point $P_{13b}$ in which each of 26 springs that may be connected between the fixed body 140 and the moving body 170 is coupled to the fixed body 140, are shown.

The first A-point $P_{1a}$ is positioned at a coordinate (0, 1, 1) that is the center of one corner of the fixed body 140 having the regular hexahedral shape. A spring connected to the first A-point $P_{1a}$ will be referred to as a first A-spring having a modulus of elasticity $k_{1a}$, and a distance between the original point O and the first A-point $P_{1a}$ will be referred to as $l_{1a}$.

The second B-point $P_{1b}$ is positioned at a coordinate (0, −1, −1) that is the center of one corner of the fixed body 140 having the regular hexahedral shape. A spring connected to the first B-point $P_{1b}$ will be referred to as a first B-spring having a modulus of elasticity $k_{1b}$, and a distance between the original point O and the first B-point $P_{1b}$ will be referred to as $l_{1b}$.

The second A-point $P_{2a}$ is positioned at a coordinate (−1, 0, 1) that is the center of one corner of the fixed body 140 having the regular hexahedral shape. A spring connected to the second A-point $P_{2a}$ will be referred to as a second A-spring having a modulus of elasticity $k_{2a}$, and a distance between the original point O and the second A-point $P_{2a}$ will be referred to as $l_{2a}$.

The second B-point $P_{2b}$ is positioned at a coordinate (1, 0, −1) that is the center of one corner of the fixed body 140 having the regular hexahedral shape. A spring connected to the second B-point $P_{2b}$ will be referred to as a second B-spring having a modulus of elasticity $k_{2b}$, and a distance between the original point O and the second B-point $P_{2b}$ will be referred to as $l_{2b}$.

The third A-point $P_{3a}$ is positioned at a coordinate (0, −1, 1) that is the center of one corner of the fixed body 140 having the regular hexahedral shape. A spring connected to the third A-point $P_{1a}$ will be referred to as a third A-spring having a modulus of elasticity $k_{3a}$, and a distance between the original point O and the third A-point $P_{1a}$ will be referred to as $l_{3a}$.

The third B-point $P_{3b}$ is positioned at a coordinate (0, 1, −1) that is the center of one corner of the fixed body 140 having the regular hexahedral shape. A spring connected to the third B-point $P_{3b}$ will be referred to as a third B-spring having a modulus of elasticity $k_{3b}$, and a distance between the original point O and the third B-point $P_{3b}$ will be referred to as $l_{3b}$.

The fourth A-point $P_{4a}$ is positioned at a coordinate (1, 0, 1) that is the center of one corner of the fixed body 140 having the regular hexahedral shape. A spring connected to the fourth A-point $P_{4a}$ will be referred to as a fourth A-spring having a modulus of elasticity $k_{4a}$, and a distance between the original point O and the fourth A-point $P_{4a}$ will be referred to as $l_{4a}$.

The fourth B-point $P_{4b}$ is positioned at a coordinate (−1, 0, −1) that is the center of one corner of the fixed body 140 having the regular hexahedral shape. A spring connected to the fourth B-point $P_{4b}$ will be referred to as a fourth B-spring having a modulus of elasticity $k_{4b}$, and a distance between the original point O and the fourth B-point $P_{4b}$ will be referred to as $l_{4b}$.

The fifth A-point $P_{5a}$ is positioned at a coordinate (1, 1, 1) that is the center of one corner of the fixed body 140 having the regular hexahedral shape. A spring connected to the fifth A-point $P_{5a}$ will be referred to as a fifth A-spring having a modulus of elasticity $k_{5a}$, and a distance between the original point O and the fifth A-point $P_{sa}$ will be referred to as $l_{5a}$.

The fifth B-point $P_{5b}$ is positioned at a coordinate (−1, −1, −1) that is the center of one corner of the fixed body 140 having the regular hexahedral shape. A spring connected to the fifth B-point $P_{5b}$ will be referred to as a fifth B-spring having a modulus of elasticity $k_{5b}$, and a distance between the original point O and the fifth B-point $P_{5b}$ will be referred to as $l_{5b}$.

The sixth A-point $P_{6a}$ is positioned at a coordinate (−1, 1, 1) that is the center of one corner of the fixed body 140 having the regular hexahedral shape. A spring connected to the sixth A-point $P_{6a}$ will be referred to as a sixth A-spring having a modulus of elasticity $k_{6a}$, and a distance between the original point O and the sixth A-point $P_{6a}$ will be referred to as $l_{6a}$.

The sixth B-point $P_{6b}$ is positioned at a coordinate (1, −1, −1) that is the center of one corner of the fixed body 140 having the regular hexahedral shape. A spring connected to the sixth B-point $P_{6b}$ will be referred to as a sixth B-spring having a modulus of elasticity $k_{6b}$, and a distance between the original point O and the sixth B-point $P_{6b}$ will be referred to as $l_{6b}$.

The seventh A-point $P_{7a}$ is positioned at a coordinate (−1, −1, 1) that is the center of one corner of the fixed body 140 having the regular hexahedral shape. A spring connected to the seventh A-point $P_{7a}$ will be referred to as a seventh A-spring having a modulus of elasticity $k_{7a}$, and a distance between the original point O and the seventh A-point $P_{7a}$ will be referred to as $l_{7a}$.

The seventh B-point $P_{7b}$ is positioned at a coordinate (1, 1, −1) that is the center of one corner of the fixed body 140 having the regular hexahedral shape. A spring connected to the seventh B-point $P_{7b}$ will be referred to as a seventh B-spring having a modulus of elasticity $k_{7b}$, and a distance between the original point O and the seventh B-point $P_{7b}$ will be referred to as $l_{7b}$.

The eighth A-point $P_{8a}$ is positioned at a coordinate (1, −1, 1) that is the center of one corner of the fixed body 140 having the regular hexahedral shape. A spring connected to the eighth A-point $P_{8a}$ will be referred to as an eighth A-spring having a modulus of elasticity $k_{8a}$, and a distance between the original point O and the eighth A-point $P_{8a}$ will be referred to as $l_{8a}$.

The eighth B-point $P_{8b}$ is positioned at a coordinate (−1, 1, −1) that is the center of one corner of the fixed body 140 having the regular hexahedral shape. A spring connected to the eighth B-point $P_{8b}$ will be referred to as an eighth B-spring having a modulus of elasticity $k_{8b}$, and a distance between the original point O and the eighth B-point $P_{8b}$ will be referred to as $l_{8b}$.

The ninth A-point $P_{9a}$ is positioned at a coordinate (1, 1, 0) that is the center of one corner of the fixed body 140 having the regular hexahedral shape. A spring connected to the ninth A-point $P_{9a}$ will be referred to as a ninth A-spring having a modulus of elasticity $k_{9a}$, and a distance between the original point O and the ninth A-point $P_{9a}$ will be referred to as $l_{9a}$.

The ninth B-point $P_{9b}$ is positioned at a coordinate (−1, −1, 0) that is the center of one corner of the fixed body 140 having the regular hexahedral shape. A spring connected to the ninth B-point $P_{9b}$ will be referred to as a ninth B-spring having a modulus of elasticity $k_{9b}$, and a distance between the original point O and the ninth B-point $P_{9b}$ will be referred to as $l_{9b}$.

The tenth A-point $P_{10a}$ is positioned at a coordinate (−1, 1, 0) that is the center of one corner of the fixed body 140 having the regular hexahedral shape. A spring connected to the ninth A-point $P_{9a}$ will be referred to as a tenth A-spring having a modulus of elasticity $k_{10a}$, and a distance between the original point O and the tenth A-point $P_{10a}$ will be referred to as $l_{10a}$.

The tenth B-point $P_{10b}$ is positioned at a coordinate (1, −1, 0) that is the center of one corner of the fixed body 140 having the regular hexahedral shape. A spring connected to the tenth B-point $P_{10b}$ will be referred to as a tenth B-spring having a modulus of elasticity $k_{10b}$, and a distance between the original point O and the tenth B-point $P_{10b}$ will be referred to as $l_{10b}$.

The eleventh A-point $P_{11a}$ is positioned at a coordinate (0, 1, 0) that is the center of one corner of the fixed body 140 having the regular hexahedral shape. A spring connected to the eleventh A-point $P_{11a}$ will be referred to as an eleventh A-spring having a modulus of elasticity $k_{11a}$, and a distance between the original point O and the eleventh A-point $P_{11a}$ will be referred to as $l_{11a}$.

The eleventh B-point $P_{11b}$ is positioned at a coordinate (0, −1, 0) that is the center of one corner of the fixed body 140 having the regular hexahedral shape. A spring connected to the eleventh B-point $P_{11b}$ will be referred to as a tenth B-spring having a modulus of elasticity $k_{11b}$, and a distance between the original point O and the eleventh B-point $P_{11b}$ will be referred to as $l_{11b}$.

The twelfth A-point $P_{12a}$ is positioned at a coordinate (−1, 0, 0) that is the center of one corner of the fixed body 140 having the regular hexahedral shape. A spring connected to the twelfth A-point $P_{12a}$ will be referred to as a twelfth A-spring having a modulus of elasticity $k_{12a}$, and a distance between the original point O and the twelfth A-point $P_{12a}$ will be referred to as $l_{12a}$.

The twelfth B-point $P_{12b}$ is positioned at a coordinate (1, 0, 0) that is the center of one corner of the fixed body 140 having the regular hexahedral shape. A spring connected to the twelfth B-point $P_{12b}$ will be referred to as a twelfth B-spring having a modulus of elasticity $k_{12b}$, and a distance between the original point O and the twelfth B-point $P_{12b}$ will be referred to as $l_{12b}$.

The thirteenth A-point $P_{13a}$ is positioned at a coordinate (0, 0, 1) that is the center of one corner of the fixed body 140 having the regular hexahedral shape. A spring connected to the thirteenth A-point $P_{13a}$ will be referred to as a thirteenth A-spring having a modulus of elasticity $k_{13a}$, and a distance between the original point O and the thirteenth A-point $P_{13a}$ will be referred to as $l_{13a}$.

The thirteenth B-point $P_{13b}$ is positioned at a coordinate (0, 0, −1) that is the center of one corner of the fixed body 140 having the regular hexahedral shape. A spring connected to the thirteenth B-point $P_{13b}$ will be referred to as a thirteenth B-spring having a modulus of elasticity $k_{13b}$, and a distance between the original point O and the thirteenth B-point $P_{13b}$ will be referred to as $l_{13a}$.

A 3D equation of motion through the configuration described above with reference to FIG. 3 may be expressed by the following matrix equation of Equation 1.

$$F = K_{sa}D, \qquad (1)$$

where $$F = \begin{bmatrix} F_x \\ F_y \\ F_z \end{bmatrix}, \quad K_{sa} = \begin{bmatrix} k_{11,sa} & k_{12,sa} & k_{13,sa} \\ k_{21,sa} & k_{22,sa} & k_{23,sa} \\ k_{31,sa} & k_{32,sa} & k_{33,sa} \end{bmatrix}, \quad D = \begin{bmatrix} x \\ y \\ z \end{bmatrix}$$

F is a 3D force matrix applied to the moving body 140, D is a 3D displacement matrix of the moving body 140, and $K_{sa}$ is a stiffness matrix.

$k_{11,sa}$ in $K_{sa}$ will be obtained by the following Equation 2.

$$k_{11,sa} = k_{1a} + k_{1b} + k_{2a} + k_{2b} + k_{3a} + k_{3b} + k_{4a} + k_{4b} + \qquad (2)$$
$$k_{5a} + k_{5b} + k_{6a} + k_{6b} + k_{7a} + k_{7b} + k_{8a} + k_{8b} + k_{9a} + k_{9b} +$$
$$k_{10a} + k_{10b} + k_{11a} + k_{11b} + k_{12a} + k_{12b} + k_{13a} + k_{13b} -$$
$$\frac{1}{l}\left(\frac{k_{1a}l_{1a}}{\sqrt{2}} + \frac{k_{1b}l_{1b}}{\sqrt{2}} + \frac{k_{2a}l_{2a}}{2\sqrt{2}} + \frac{k_{2b}l_{2b}}{2\sqrt{2}} + \frac{k_{3a}l_{3a}}{\sqrt{2}} + \frac{k_{3b}l_{3}}{\sqrt{2}} + \frac{k_{4a}l_{4a}}{2\sqrt{2}} + \right.$$
$$\frac{k_{4b}l_{4b}}{2\sqrt{2}} + \frac{2k_{5a}l_{5a}}{3\sqrt{3}} + \frac{2k_{5b}l_{5b}}{3\sqrt{3}} + \frac{2k_{6a}l_{6a}}{3\sqrt{3}} + \frac{2k_{6b}l_{6b}}{3\sqrt{3}} + \frac{2k_{7a}l_{7a}}{3\sqrt{3}} +$$
$$\frac{2k_{7b}l_{7b}}{3\sqrt{3}} + \frac{2k_{8a}l_{8a}}{3\sqrt{3}} + \frac{2k_{8b}l_{8b}}{3\sqrt{3}} + \frac{k_{9a}l_{9a}}{2\sqrt{2}} + \frac{k_{9b}l_{9b}}{2\sqrt{2}} + \frac{k_{10a}l_{10a}}{2\sqrt{2}} +$$
$$\left. \frac{k_{10b}l_{10b}}{2\sqrt{2}} + k_{11a}l_{11a} + k_{11b}l_{11b} + k_{13a}l_{13a} + k_{13b}l_{13b} \right)$$

$k_{22,sa}$ in $K_{sa}$ will be obtained by the following Equation 3.

$$k_{22,sa} = k_{1a} + k_{1b} + k_{2a} + k_{2b} + k_{3a} + k_{3b} + k_{4a} + k_{4b} + \qquad (3)$$
$$k_{5a} + k_{5b} + k_{6a} + k_{6b} + k_{7a} + k_{7b} + k_{8a} + k_{8b} + k_{9a} + k_{9b} +$$
$$k_{10a} + k_{10b} + k_{11a} + k_{11b} + k_{12a} + k_{12b} + k_{13a} + k_{13b} -$$
$$\frac{1}{l}\left(\frac{k_{1a}l_{1a}}{2\sqrt{2}} + \frac{k_{1b}l_{1b}}{2\sqrt{2}} + \frac{k_{2a}l_{2a}}{\sqrt{2}} + \frac{k_{2b}l_{2b}}{\sqrt{2}} + \frac{k_{3a}l_{3a}}{2\sqrt{2}} + \frac{k_{3b}l_{3}}{2\sqrt{2}} + \frac{k_{4a}l_{4a}}{\sqrt{2}} + \right.$$
$$\frac{k_{4b}l_{4b}}{\sqrt{2}} + \frac{2k_{5a}l_{5a}}{3\sqrt{3}} + \frac{2k_{5b}l_{5b}}{3\sqrt{3}} + \frac{2k_{6a}l_{6a}}{3\sqrt{3}} + \frac{2k_{6b}l_{6b}}{3\sqrt{3}} + \frac{2k_{7a}l_{7a}}{3\sqrt{3}} +$$
$$\frac{2k_{7b}l_{7b}}{3\sqrt{3}} + \frac{2k_{8a}l_{8a}}{3\sqrt{3}} + \frac{2k_{8b}l_{8b}}{3\sqrt{3}} + \frac{k_{9a}l_{9a}}{2\sqrt{2}} + \frac{k_{9b}l_{9b}}{2\sqrt{2}} + \frac{k_{10a}l_{10a}}{2\sqrt{2}} +$$
$$\left. \frac{k_{10b}l_{10b}}{2\sqrt{2}} + k_{12a}l_{12a} + k_{12b}l_{12b} + k_{13a}l_{13a} + k_{13b}l_{13b} \right)$$

$k_{33,sa}$ in $K_{sa}$ will be obtained by the following Equation 4.

$$k_{33,sa} = k_{1a} + k_{1b} + k_{2a} + k_{2b} + k_{3a} + k_{3b} + k_{4a} + k_{4b} + \qquad (4)$$
$$k_{5a} + k_{5b} + k_{6a} + k_{6b} + k_{7a} + k_{7b} + k_{8a} + k_{8b} + k_{9a} + k_{9b} +$$
$$k_{10a} + k_{10b} + k_{11a} + k_{11b} + k_{12a} + k_{12b} + k_{13a} + k_{13b} -$$
$$\frac{1}{l}\left(\frac{k_{1a}l_{1a}}{2\sqrt{2}} + \frac{k_{1b}l_{1b}}{2\sqrt{2}} + \frac{k_{2a}l_{2a}}{2\sqrt{2}} + \frac{k_{2b}l_{2b}}{2\sqrt{2}} + \frac{k_{3a}l_{3a}}{2\sqrt{2}} + \frac{k_{3b}l_{3}}{2\sqrt{2}} + \frac{k_{4a}l_{4a}}{2\sqrt{2}} + \right.$$
$$\frac{k_{4b}l_{4b}}{2\sqrt{2}} + \frac{2k_{5a}l_{5a}}{3\sqrt{3}} + \frac{2k_{5b}l_{5b}}{3\sqrt{3}} + \frac{2k_{6a}l_{6a}}{3\sqrt{3}} + \frac{2k_{6b}l_{6b}}{3\sqrt{3}} + \frac{2k_{7a}l_{7a}}{3\sqrt{3}} +$$
$$\frac{2k_{7b}l_{7b}}{3\sqrt{3}} + \frac{2k_{8a}l_{8a}}{3\sqrt{3}} + \frac{2k_{8b}l_{8b}}{3\sqrt{3}} + \frac{k_{9a}l_{9a}}{\sqrt{2}} + \frac{k_{9b}l_{9b}}{\sqrt{2}} + \frac{k_{10a}l_{10a}}{\sqrt{2}} +$$
$$\left. \frac{k_{10b}l_{10b}}{\sqrt{2}} + k_{11a}l_{11a} + k_{11b}l_{11b} + k_{12a}l_{12a} + k_{12b}l_{12b} \right)$$

$k_{12,sa}$ and $k_{21,sa}$ in $K_{sa}$ will be obtained by the following Equation 5.

$$k_{12,sa} = \qquad (5)$$
$$k_{21,sa} = \left(\frac{1}{l}\right)\left(\frac{k_{5a}l_{5a}}{3\sqrt{3}} + \frac{k_{5b}l_{5b}}{3\sqrt{3}} + \frac{k_{7a}l_{7a}}{3\sqrt{3}} + \frac{k_{7b}l_{7b}}{3\sqrt{3}} + \frac{k_{9a}l_{9a}}{2\sqrt{2}} + \frac{k_{9b}l_{9b}}{2\sqrt{2}}\right) -$$
$$\left(\frac{1}{l}\right)\left(\frac{k_{6a}l_{6a}}{3\sqrt{3}} + \frac{k_{6b}l_{6b}}{3\sqrt{3}} + \frac{k_{8a}l_{8a}}{3\sqrt{3}} + \frac{k_{8b}l_{8b}}{3\sqrt{3}} + \frac{k_{10a}l_{10a}}{2\sqrt{2}} + \frac{k_{10b}l_{10b}}{2\sqrt{2}}\right)$$

$k_{13,sa}$ and $k_{31,sa}$ in $K_{sa}$ will be obtained by the following Equation 6.

$$k_{13,sa} = \qquad (6)$$
$$k_{31,sa} = \left(\frac{1}{l}\right)\left(\frac{k_{4a}l_{4a}}{2\sqrt{2}} + \frac{k_{4b}l_{4b}}{2\sqrt{2}} + \frac{k_{5a}l_{5a}}{3\sqrt{3}} + \frac{k_{5b}l_{5b}}{3\sqrt{3}} + \frac{k_{8a}l_{8a}}{3\sqrt{3}} + \frac{k_{8b}l_{8b}}{3\sqrt{3}}\right) -$$
$$\left(\frac{1}{l}\right)\left(\frac{k_{2a}l_{2a}}{2\sqrt{2}} + \frac{k_{2b}l_{2b}}{2\sqrt{2}} + \frac{k_{6a}l_{6a}}{3\sqrt{3}} + \frac{k_{6b}l_{6b}}{3\sqrt{3}} + \frac{k_{7a}l_{7a}}{3\sqrt{3}} + \frac{k_{7b}l_{7b}}{3\sqrt{3}}\right)$$

$k_{23,sa}$ and $k_{32,sa}$ in $K_{sa}$ will be obtained by the following Equation 7.

$$k_{23,sa} = \qquad (7)$$
$$k_{32,sa} = \left(\frac{1}{l}\right)\left(\frac{k_{1a}l_{1a}}{2\sqrt{2}} + \frac{k_{1b}l_{1b}}{2\sqrt{2}} + \frac{k_{5a}l_{5a}}{3\sqrt{3}} + \frac{k_{5b}l_{5b}}{3\sqrt{3}} + \frac{k_{6a}l_{6a}}{3\sqrt{3}} + \frac{k_{6b}l_{6b}}{3\sqrt{3}}\right) -$$
$$\left(\frac{1}{l}\right)\left(\frac{k_{3a}l_{3a}}{2\sqrt{2}} + \frac{k_{3b}l_{3b}}{2\sqrt{2}} + \frac{k_{7a}l_{7a}}{3\sqrt{3}} + \frac{k_{7b}l_{7b}}{3\sqrt{3}} + \frac{k_{8a}l_{8a}}{3\sqrt{3}} + \frac{k_{8b}l_{8b}}{3\sqrt{3}}\right)$$

In order to minimize numerical errors when reliability and accuracy verification is performed, a difference between diagonal elements ($k_{11,sa}$, $k_{22,sa}$, $k_{33,sa}$) and non-diagonal elements ($k_{12,sa}$, $k_{13,sa}$, $k_{21,sa}$, $k_{23,sa}$, $k_{31,sa}$, $k_{33,sa}$) in $K_{sa}$ needs to be minimized. To this end, first, only moduli of elasticity having only one coefficient sign among moduli of elasticity used in the non-diagonal elements of $K_{sa}$ are selected. That is, only moduli of elasticity having only one coefficient sign of a positive number (+) and a negative number (−) are selected. This is because, when moduli of elasticity having coefficient signs of both the positive number (+) and the negative number (−) are simultaneously used, the effects on the non-diagonal elements are offset, that is, the non-diagonal elements are close to 0, so that the difference between the diagonal elements and the non-diagonal elements may be increased. That is, because moduli of elasticity $k_{6a}$, $k_{6b}$, $k_{7a}$, $k_{7b}$, $k_{8a}$, and $k_{8b}$ in the non-diagonal elements ($k_{12,sa}$, $k_{13,sa}$, $k_{21,sa}$, $k_{23,sa}$, $k_{31,sa}$, $k_{33,sa}$) have both a positive coefficient and a negative coefficient, the sixth A-spring, the sixth B-spring, the seventh A-spring, the seventh B-spring, the eighth A-spring, and the eighth B-spring, which correspond to the moduli of elasticity $k_{6a}$, $k_{6b}$, $k_{7a}$, $k_{7b}$, $k_{8a}$, and $k_{8b}$, are excluded from the first A-spring, the first B-spring, the second A-spring, the second B-spring, the third A-spring, the third B-spring, the fourth A-spring, the fourth B-spring, the fifth A-spring, the fifth B-spring, the sixth A-spring, the sixth B-spring, the seventh A-spring, the seventh B-spring, the eighth A-spring, the eighth B-spring, the ninth A-spring, the ninth B-spring, the tenth A-spring, and the tenth B-spring, which are springs related to the moduli of elasticity used in the non-diagonal elements, and the remaining first A-spring, the first B-spring, the second A-spring, the second B-spring, the third A-spring, the third B-spring, the fourth A-spring, the fourth B-spring, the fifth A-spring, the fifth B-spring, the ninth A-spring, the ninth B-spring, the tenth A-spring, and the tenth B-spring are excluded.

Next, only springs that correspond to the moduli of elasticity having only positive coefficients are selected from the selected first A-spring, the first B-spring, the second A-spring, the second B-spring, the third A-spring, the third B-spring, the fourth A-spring, the fourth B-spring, the fifth A-spring, the fifth B-spring, the ninth A-spring, the ninth B-spring, the tenth A-spring, and the tenth B-spring so as to reduce the difference between the diagonal elements and the non-diagonal elements. Finally, eight springs, i.e., the first A-spring, the first B-spring, the fourth A-spring, the fourth B-spring, the fifth A-spring, the fifth B-spring, the ninth A-spring, and the ninth B-spring that correspond to the moduli of elasticity $k_{1a}$, $k_{1b}$, $k_{4a}$, $k_{4b}$, $k_{5a}$, $k_{5b}$, $k_{9a}$, and $k_{9b}$ having the positive coefficients excluding $k_{2a}$, $k_{2b}$, $k_{3a}$, $k_{3b}$, $k_{10a}$, and $k_{10b}$ having the negative coefficients are selected. The selected first A-spring corresponds to the first spring 101a illustrated in FIG. 1, the selected first B-spring corresponds to the second spring 101b illustrated in FIG. 1, the selected fourth A-spring corresponds to the third spring 104a illustrated in FIG. 1, the selected fourth B-spring corresponds to the fourth spring 104b illustrated in FIG. 1, the selected fifth A-spring corresponds to the fifth spring 105a illustrated in FIG. 1, the selected fifth B-spring corresponds to the sixth spring 105b illustrated in FIG. 1, the selected ninth A-spring corresponds to the seventh spring 109a illustrated in FIG. 1, and the selected ninth B-spring corresponds to the eighth spring 109b illustrated in FIG. 1.

In the above-described embodiment, the 3D spring array device 100 includes all of eight springs 101a, 101b, 104a, 104b, 105a, 105b, 109a, and 109b. However, the present invention is not limited thereto. At least one of the eight springs 0101a, 101b, 104a, 104b, 105a, 105b, 109a, and 109b selected in the above-described procedures may be selected and used, which also belongs to the scope of the present invention. This is because each of the selected eight springs 101a, 101b, 104a, 104b, 105a, 105b, 109a, and 109b has only one coefficient sign that is a condition of selecting springs described above and satisfies that the coefficient sign has a positive number. That is, according to the present invention, at least one selected from the group consisting of the eight springs 101a, 101b, 104a, 104b, 105a, 105b, 109a, and 109b may be provided.

As described above, according to the present invention, all of the objectives of the present invention described above can be achieved. In detail, a device connected to an end effector of a mechanical impedance estimating robot so as to verify the reliability and accuracy of the mechanical impedance estimating robot includes a fixed body having an internal space therein, a moving body in the internal space, and eight springs for connecting the fixed body to the moving body in the internal space with an optimum combination so that a difference between diagonal elements and non-diagonal elements of a stiffness matrix used in numerical calculation is reduced and thus numerical errors can be minimized.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A three-dimensional (3D) spring array device that is fastenable to an end effector of a mechanical impedance estimating robot so as to verify reliability and accuracy of the mechanical impedance estimating robot, the 3D spring array device comprising:
   a fixed body having an internal space therein;
   a moving body positioned in a center of an x-y-z orthogonal coordinate system in the internal space, wherein the moving body is configured to be fastenable to the end effector of the mechanical impedance estimating robot; and
   a first spring, a second spring, a third spring, a fourth spring, a fifth spring, a sixth spring, a seventh spring, and an eighth spring and configured to connect the fixed body to the moving body in the internal space,
   wherein each of the first spring and the second spring is positioned to extend along a first straight line that passes through a coordinate (0, a, a) and a coordinate (0, −a, −a) in the x-y-z orthogonal coordinate system, and the first spring and the second spring are positioned at opposite sides with the moving body therebetween, and
   each of the third spring and the fourth spring is positioned to extend along a second straight line that passes through a coordinate (a, 0, a) and a coordinate (−a, 0, −a) in the x-y-z orthogonal coordinate system, and the third spring and the fourth spring are positioned at opposite sides with the moving body therebetween, and
   each of the fifth spring and the sixth spring is positioned to extend along a third straight line that passes through a coordinate (a, a, a) and a coordinate (−a, −a, −a) in the x-y-z orthogonal coordinate system, and the fifth spring and the sixth spring are positioned at opposite sides with the moving body therebetween, and
   each of the seventh spring and the eighth spring is positioned to extend along a fourth straight line that passes through a coordinate (a, a, 0) and a coordinate (−a, −a, 0) in the x-y-z orthogonal coordinate system, and the seventh spring and the eighth spring are positioned at opposite sides with the moving body therebetween and wherein the 3D spring array device does not comprise additional springs configured to connect the fixed body to the moving body other than the first, second, third, fourth, fifth, sixth, seventh, and eighth springs.

2. The 3D spring array device of claim 1, wherein the first spring is coupled to the fixed body at the coordinate (0, a, a), the second spring is coupled to the fixed body at the coordinate (0, −a, −a), the third spring is coupled to the fixed body at the coordinate (a, 0, a), the fourth spring is coupled to the fixed body at the coordinate (−a, 0, −a), the fifth spring is coupled to the fixed body at the coordinate (a, a, a), the sixth spring is coupled to the fixed body at the coordinate (−a, −a, −a), the seventh spring is coupled to the fixed body at the coordinate (a, a, 0), and the eighth spring is coupled to the fixed body at the coordinate (−a, −a, 0).

3. The 3D spring array device of claim 2, wherein the fixed body has a frame structure comprising at least part of a regular hexahedral frame shape based on the moving body, and the fifth spring coupling coordinate and the sixth spring coupling coordinate are at two vertices that are symmetrical with each other based on the moving body in the regular hexahedron, and each of the first spring coupling coordinate, the third spring coupling coordinate, and the seventh spring coupling coordinate is in a center of three corners each being connected to one of the two vertices at which the fifth spring coupling coordinate is located, and each of the second spring coupling coordinate, the fourth spring coupling coordinate, and the eighth spring coupling coordinate is positioned in a center of the three corners each being connected to the other one of the two vertices at which the sixth spring coupling coordinate is located.

4. The 3D spring array device of claim 1, wherein a bolt hole for bolt fastening with the end effector is formed in the moving body.

5. The 3D spring array device of claim 4, wherein the moving body is hollow.

6. The 3D spring array device of claim 4, wherein an opening to access the bolt hole is formed in the moving body.

7. A three-dimensional (3D) spring array device that is fastenable to an end effector of a mechanical impedance estimating robot so as to verify reliability and accuracy of the mechanical impedance estimating robot, the 3D spring array device comprising:

a fixed body having an internal space therein;

a moving body positioned in the internal space, wherein the moving body is configured to be fastenable to the end effector of the mechanical impedance estimating robot; and a first spring, a second spring, a third spring, a fourth spring, a fifth spring, a sixth spring, a seventh spring, and an eighth spring configured to connect the fixed body to the moving body in the internal space, wherein the first spring is coupled to the fixed body at a first coupling coordinate, the second spring is coupled to the fixed body at a second coupling coordinate, the third spring is coupled to the fixed body at a third coupling coordinate, the fourth spring is coupled to the fixed body at a fourth coupling coordinate, the fifth spring is coupled to the fixed body at a fifth coupling coordinate, the sixth spring is coupled to the fixed body at a sixth coupling coordinate, the seventh spring is coupled to the fixed body at a seventh coupling coordinate, and the eighth spring is coupled to the fixed body at an eighth coupling coordinate, and the fifth spring coupling coordinate and the sixth spring coupling coordinate are positioned at two vertices that are symmetrical with each other with respect to the moving body in a regular hexahedron based on the moving body, and each of the first spring coupling coordinate, the third spring coupling coordinate, and the seventh spring coupling coordinate is positioned in a center of three corners each being connected to one of the two vertices at which the fifth spring coupling coordinate is positioned in the regular hexahedron, and each of the second spring coupling coordinate, the fourth spring coupling coordinate, and the eighth spring coupling coordinate is positioned in a center of the three corners each being connected to the other one of the two vertices at which the sixth spring coupling coordinate is positioned in the regular hexahedron, and wherein the 3D spring array device does not comprise additional springs configured to connect the fixed body to the moving body other than the first, second, third, fourth, fifth, sixth, seventh, and eighth springs.

* * * * *